United States Patent
Neef et al.

(10) Patent No.: US 6,790,843 B1
(45) Date of Patent: Sep. 14, 2004

(54) C-19-HALOGEN-SUBSTITUTED STEROIDS OF THE ANDROST-9(11)-ENE-SERIES, METHODS FOR THE PRODUCTION AND USE THEREOF

(75) Inventors: Gunter Neef, Berlin (DE); Roland Golde, Bergfelde (DE); Karl-Heinrich Fritzemeier, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/031,198
(22) PCT Filed: Jul. 17, 2000
(86) PCT No.: PCT/DE00/02390
§ 371 (c)(1), (2), (4) Date: Jul. 2, 2002
(87) PCT Pub. No.: WO01/05805
PCT Pub. Date: Jan. 25, 2001

(30) Foreign Application Priority Data

Jul. 15, 1999 (DE) .......................................... 199 34 088

(51) Int. Cl.$^7$ .............................. A61K 31/56; C07J 1/00
(52) U.S. Cl. ....................................... 514/182; 552/633
(58) Field of Search ........................... 514/182; 552/633

(56) References Cited

U.S. PATENT DOCUMENTS

| | | |
|---|---|---|
| 3,101,356 A | 8/1963 | Bowers |
| 5,218,110 A | 6/1993 | Weintraub |
| 5,318,961 A | 6/1994 | Weintraub et al. |
| 5,436,237 A | 7/1995 | Weintraub et al. |

OTHER PUBLICATIONS

Herbst et al. "Totally Synthetic Steroid Hormones, XVIII. DL–17. beta.–Hydroxy–18–methylandrosta–4, 9(11)–dien–3–one and dl–18–methyl–5.alpha.–androstan–3, 17–dione", STEROIDS, Jun. 6, 1968, vol. 11, No. 6, pp. 935–943.

Schmit J–P et al., "The Anderson Receptor Binding Site a Conformational Study of Steroids in Relation with Their Affinity 1. Interaction with the D Ring" *Journal of Steroid Biochemistry*, 1980, vol. 13, No. 12, pp. 1387–1394.

Kirchoff et al., "Differences in the Steroid Binding Site Specificities of Rat Prostate Androgen Receptor and Epididymal Androgen Binding Protein", *Journal of Steroid Biochemistry*, 1979, vol. 10, No. 5, pp. 487–498.

G. Neef et al., "A Radical Approach to the synthesis of 9(10–>10)abeo–steroids" *TETRAHEDRON*, Jan. 22, 1993, vol. 49, No. 4, pp. 833–840.

Yates et al., "Inhibitors of human adrenal C17–20 lyase and C19–5–ene, 3 beta–hydroxysteroid dehydrogenase" *J. Steroid Biochem*, 1975, vol. 6, No. 9, 1325–1327.

Goldman et al., "Effects of New Multi–Site Hormone Blockers on the Fertility of Male Rats", *Journal of Endocrinology*, Apr. 1, 1976, vol. 69, No. 1, pp. 11–21.

Kincl et al., "Pituitary gonadotropin inhibitory action of neutral steroids", *Chemical Abstracts*, Aug. 17, 1964, vol. 64, No. 4.

CN 1 174 843, Mar. 4, 1998, *Chemical Abstracts*, Abstract No. 194549, p. 616, col. 1.

Lesuisse et al., "Structure Activity Relationships of a New Family of Steroidal Aromatase Inhibitors. 1. Synthesis and Evaluation of a Series of Analogs related to 19(Methylthio)methyl androstendione (RU54115)" *J. Med.Chem*, 1996, vol. 39, No. 3, pp. 757–772.

Guarna et al., "19–Nor–10–azasteriods: A novel class of inhibitors for human steroid 5–alpha–reductases 1 and 2." *Journal of Medicinal Chemistry*, 1997, vol. 42, No. 7, pp 1112–1129.

*Primary Examiner*—Barbara P. Badio
(74) *Attorney, Agent, or Firm*—Millen White Zelano & Branigan, P.C.

(57) ABSTRACT

The invention relates to new C-19-halogen-substituted steroids of the androst-9(11)-ene series, namely 17β-hydroxy-19-halogen-androsta-4,9(11)-dien-3-ones of general formula (I) and process for their production. In addition, the use of new radiohalogen-labeled compounds of Formula (I) as radiopharmeceutical agents is the subject of the invention as well as the use of non-labeled compounds of Formula (I) as starting products for the production of new biologically active 5β-substituted androst-9(11)-enes of general formula (II) and the new 6β,19-cycloandrostadienes of Formula (III) as well as processes for their production and their use.

6 Claims, No Drawings

C-19-HALOGEN-SUBSTITUTED STEROIDS OF THE ANDROST-9(11)-ENE-SERIES, METHODS FOR THE PRODUCTION AND USE THEREOF

This application is a 371 of PCT/DE00/02390 filed Jul. 17, 2000.

The invention relates to new C-19-halogen-substituted steroids of the androst-9(11)-ene series, namely 17β-hydroxy-19-halogen-androsta-4,9(11)-dien-3-ones of general formula I, and process for their production. In addition, the use of the new radiohalogen-labeled compounds of Formula I as radio-pharmaceutical agents is the subject of the invention. These compounds can be used especially preferably in diagnostic studies of the prostate.

Moreover, the invention relates to the use of non-labeled compounds of Formula I as starting products for the production of new biologically active 5β-substituted androst-9(11)-enes of general formula II and the new 6β,19-cycloandrosta-4,9(11)-dienes of Formula III as well as processes for their production and use.

The basic attempt to develop diagnostically and therapeutically usable agents by radioactive labeling of testosterone (17β-hydroxyandrost-4-en-3-one) is known in the literature (S. J. Brandes and J. E. Katzenellenbogen, Nucl. Med. Biol. 15, 53–67, 1988). The previously used testosterone derivatives have not been introduced into clinical practice, however, in particular because of insufficient tissue selectivity and metabolic instability.

The object of this invention was therefore to find new compounds that are better suited for radiodiagnostic processes.

New 17β-hydroxy-19-halogen-androsta-4,9(11)-dien-3-ones of general formula I were found that are distinguished by a surprisingly high affinity to the androgen receptor Formula I

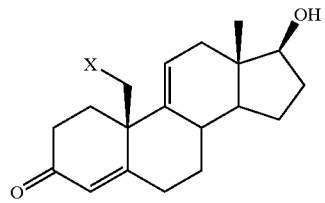

in which
X=a halogen or radiohalogen radical, preferably Br, I, $^{125}$I, $^{131}$I, $^{82}$Br or $^{77}$Br.

The compound 17β-hydroxy-19-$^{125}$iodo-androsta-4,9 (11)-dien-3-one represents a preferred radiopharmaceutical agent. The compounds 17β-hydroxy-19-iodo-androsta-4,9 (11)-dien-3-one and 19-bromo-17β-hydroxy-androsta-4,9 (11)-dien-3-one also show a high affinity to the androgen receptor.

The new compounds of general formula I are suitable in particular in the form of the radiohalogen-labeled derivatives for diagnostic use, preferably for graphic visualization of the prostate and for early detection of pathophysiological changes thereof.

The compounds according to the invention are distinguished from known derivatives of testosterone (J. N. Wright et al., J. Chem. Soc. Perkin/1989, 1647–1655) by a 9(11)-double bond. This structural element opens up the possibility of introducing a functional group at C-19 by a process that is advantageously distinguished from the standard methods for functionalizing a C-19-methyl group (J. Kalvoda et al., Helv. Chim. Acta 46, 1361, 1963 and M. Akhtar and D. H. R. Barton, J. Am. Chem. Soc. 88, 1528, 1964).

The production of the 17β-hydroxy-19-halogen-androsta-4,9(11)-dien-3-ones of general formula I according to the invention is carried out according to claim 4, and dependent claims 5 to 8 are preferred variants.

Diagram 1 below shows the synthesis methods according to the invention in the example of 17β-hydroxy-19-iodo-androsta-4,9(11)-dien-3-one.

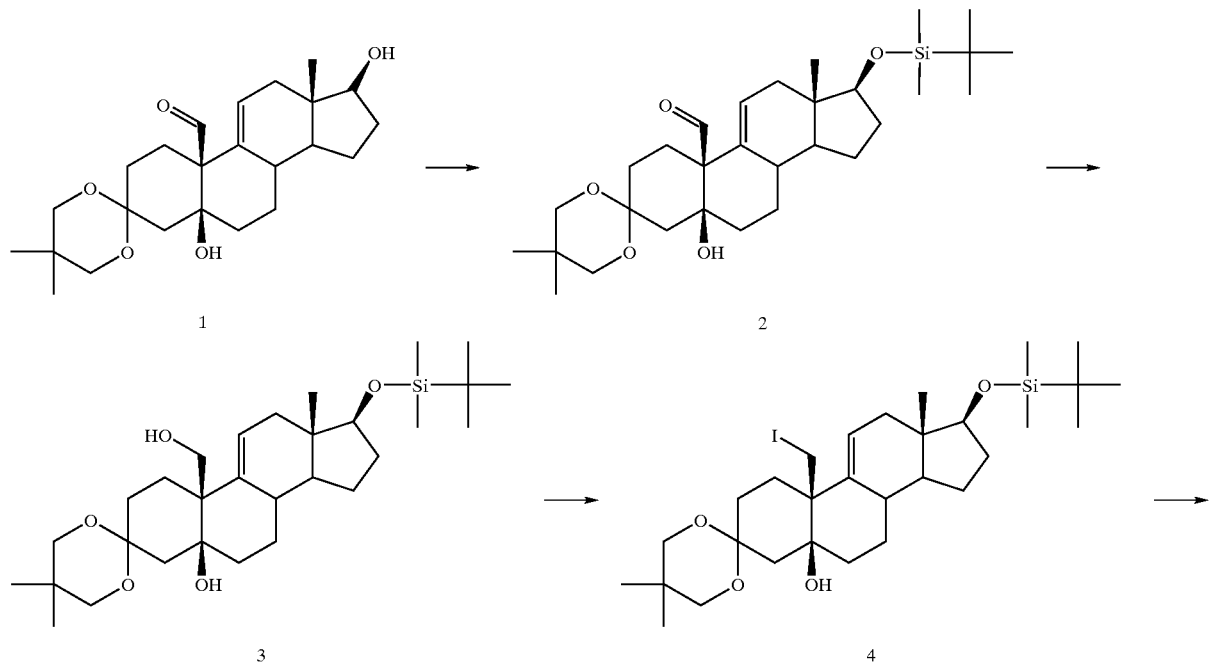

Diagram 1

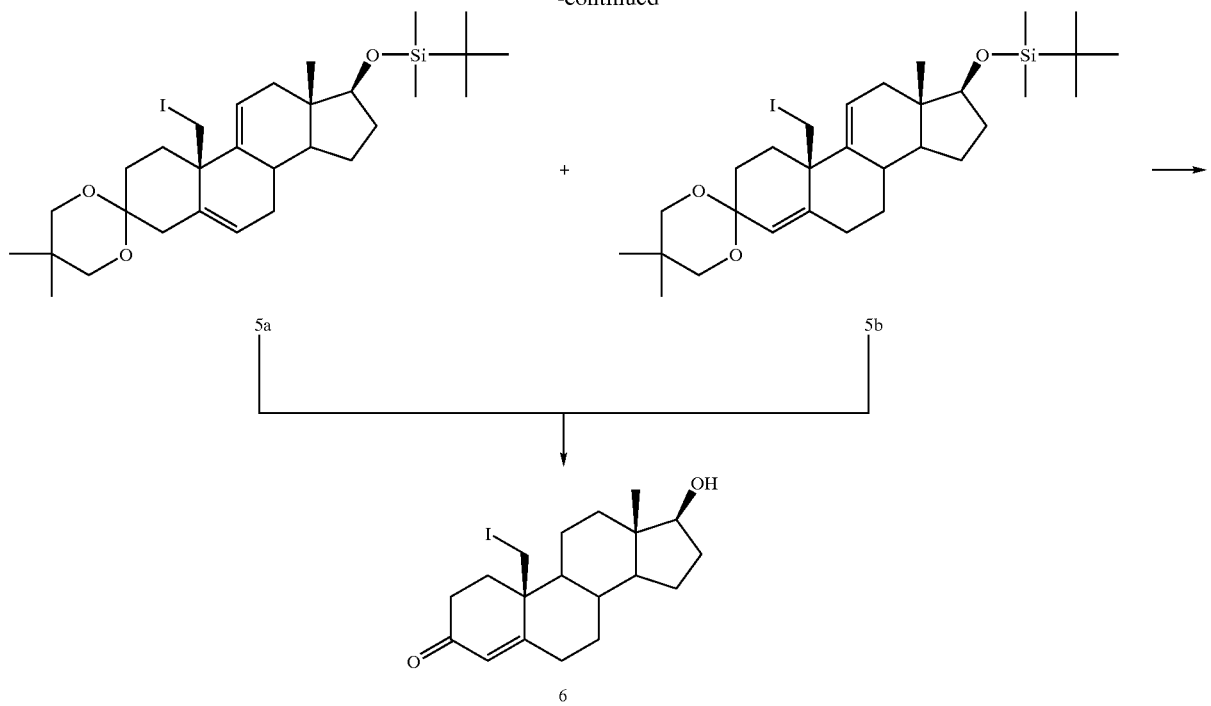

The starting material is aldehyde 1 that is known in the literature (3,3-(2,2-dimethyl-trimethylenedioxy)-10β-formyl-androst-9(11)-ene-5α,17β-diol—G. Neef et al., Tetrahedron 49, 833–840, 1993), which was used for the production of C-19-iodide 7.

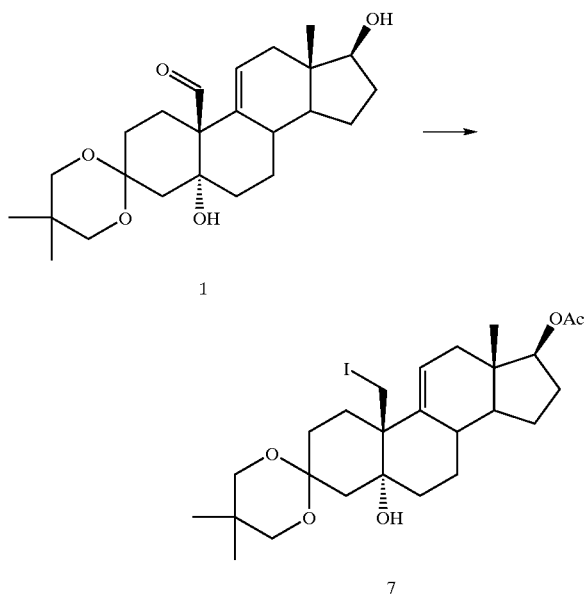

Surprisingly enough, however, the known compound 7 is not suitable for the production of an end product of Formula I according to the invention. Under the conditions of the usual deketalization/dehydration as well as the subsequent ester saponification at C-17, the C-19-iodine substitution is not maintained.

Only the process that is outlined in Diagram 1 ensures the production of the end products in high yields and purity and allows for the synthesis of the target compounds of general formula I.

In a first step of the process according to the invention, first the C-17β-hydroxy group is protected by silylation with the formation of intermediate product 2. With hydride-transferring reagents, such as, e.g., with sodium borohydride or lithium aluminum hydride, compound 2 is reduced to alcohol 3 in a way that is common in the art. Under conditions described by Neef et al. (Tetrahedron 49, 833, 1993), alcohol 3 is then further reacted to form iodide 4, whereby only a slight excess of elementary iodine must be used for reaction. Especially when the process is carried out with transfer of the reaction sequence to radiolabeled end compounds, this can be regarded as a special advantage.

Although conceivable in principle, iodide 4 cannot be converted directly into end product 6 of general formula I by treatment with acid in a one-stage process. Having the process according to the invention proceed in steps is essential to the success of the process.

First, under standard conditions (e.g., with thionyl chloride/pyridine), dehydration is performed, which results in the formation of a mixture of double-bond isomers 5a and 5b. In a separate subsequent step, mixture 5a, b is then converted smoothly into target compound 6 (Formula I with X=I) without prior separation. This final synthesis step, which contains the cleavage of the 3-ketal grouping and the silyl ether cleavage at C-17β, is preferably performed with a strong protonic acid such as trifluoroacetic acid or sulfuric acid.

The synthesis that is shown in the example of iodine for radical X of general formula I is also performed analogously for the production of bromide or the radiolabeled halides.

By the use of almost stoichiometric amounts of halogens, in particular when using radiohalogens, the process according to the invention is not only economical and environmentally safe, but it also makes possible the production of end compounds with high specific activity.

The substances of general formula I bind with high affinity to the androgen receptor despite a voluminous halogen substituent at the C-19 position.

Because of their biochemical and pharmacokinetic properties, the compounds according to the invention are extremely well suited for use in diagnostic processes.

Thus, e.g., iodide 6 (Formula I, X=I) with an $IC_{50}$ value of 57 nmol/l shows a slight weakening of the binding affinity in comparison to the reference standard ($^3$H-methyltrienolone R 1881), but it remains in an order of magnitude that shows a large degree of specific binding to the human androgen receptor in the prostate tissue.

The graphic visualization of the prostate requires, however, not only a large degree of specific binding, but it also requires little or almost no binding to transport proteins in the serum (S. J. Brandes and J. E. Katzenellenbogen, Nucl. Med. Biol. 15, 53–67, 1988). Decisive serum protein for the transport of androgens is SHBG (steroid hormone binding globulin). The SHBG affinity of iodide 6 compared to the standard DHT (5α-dihydrotestosterone) is reduced by a factor of 197. Thus, another requirement for the contrast-rich imaging of androgen-receptor-containing tissue is met.

The subject of the invention is therefore also the use of the compounds of general formula I as a diagnostic agent according to claims 9 and 10. A preferred use is carried out for graphic visualization of the prostate and for early detection of pathophysiological changes thereof.

In addition to the use for diagnostic purposes, the non-labeled compounds of Formula I according to the invention are also valuable starting products for the production of new, unusual substituted steroids according to claim 11.

The silylation of the 17β-hydroxy group of the C-19-halogen-substituted steroids of the androst-9(11)-ene series according to the invention thus results in a 17β-silyl ether of general formula Ia

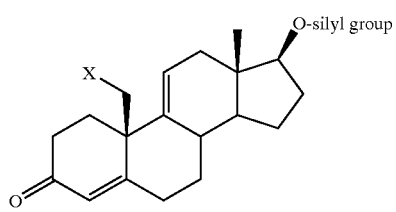

in which X=halogen, selected from Br, I, and which represents an important intermediate product for the further synthesis in a so-called tandem process to the new compounds of general formula II. Moreover, the intermediate products of formula Ia are used for the production of the new 6β,19-cycloandrosta-4,9(11)-dienes of general formula III.

Shown in the example of 17β-(tert-butyltrimethylsilyloxy)-19-iodo-androsta-4,9(11)-dien-3-one 8, the reaction with mercaptoacetic acid methyl ester in the presence of a suitable base thus results in the formation of a thia-bridged derivative 9. Starting products can also be the other non-labeled 17β-silylated C-19-halogen derivatives.

In this way, the functional group at C-19 is used to achieve a C-C linkage with the tertiary position C-5. Of course, the stereoselective introduction of functional groups in the tertiary positions of the steroid skeleton is a problem of preparative chemistry, for which general solutions are not available. Thus, specifically the introduction of a 5β-methyl group by reaction of testosterone with organometallic reagents is known (e.g., C. Petrier et al., Tetrahedron Lett. 25, 3463, 1984), but is not suitable for the introduction of higher alkyl substituents or functionally substituted alkyl groups.

Thia-bridged derivative 9 is then reacted to form compounds of general formula II with a radical R in the meaning of:
$R = -(CH_2)_n-CH_2-R^1$, $-(CH_2)_n CH_2-OR^1$,
$-(CH_2)_n-CH_2-OCOR^1$, $-(CH_2)_n-CH_2-SR^1$,
$-(CH_2)_n-CH_2-NR^{1R2}$, $-(CH_2)_n-CHO$,
$-(CH_2)_n-CN$ in which n can assume the values of 0–5, and radicals $R^1$ and $R^2$, independently of one another, stand for hydrogen or a straight-chain or branched, saturated or unsaturated hydrocarbon radical with up to 18 C atoms, whereby this radical optionally can contain additional functional groups and carbocyclic or heterocyclic ring elements.

According to the empirical findings from the normal series (9(11)-saturated) described in the literature, the result of the reaction of silylated halide Ia, e.g., iodide 8, with mercaptoacetic acid methyl ester was not predictable. As described by Halpern et al. (Steroids 4, 1–30, 1964), Santaniello and Caspi (J. Steroid Biochem. 7, 223–227, 1976) and Wright et al. (J. Chem. Soc. Perkin Trans. I, 1989, 1647–1655), the nucleophilic substitution at C-19 in the presence of the 3-oxo-4-ene structural element is extremely hampered and mainly results in skeletal restructuring.

All the more surprising is the smooth course of the reaction of a compound of Formula Ia→thia-bridged derivative 9, which can be interpreted mechanistically as a nucleophilic halogen-sulfur exchange with subsequent Michael addition (tandem process).

Diagram 2 illustrates a synthesis method by way of example:

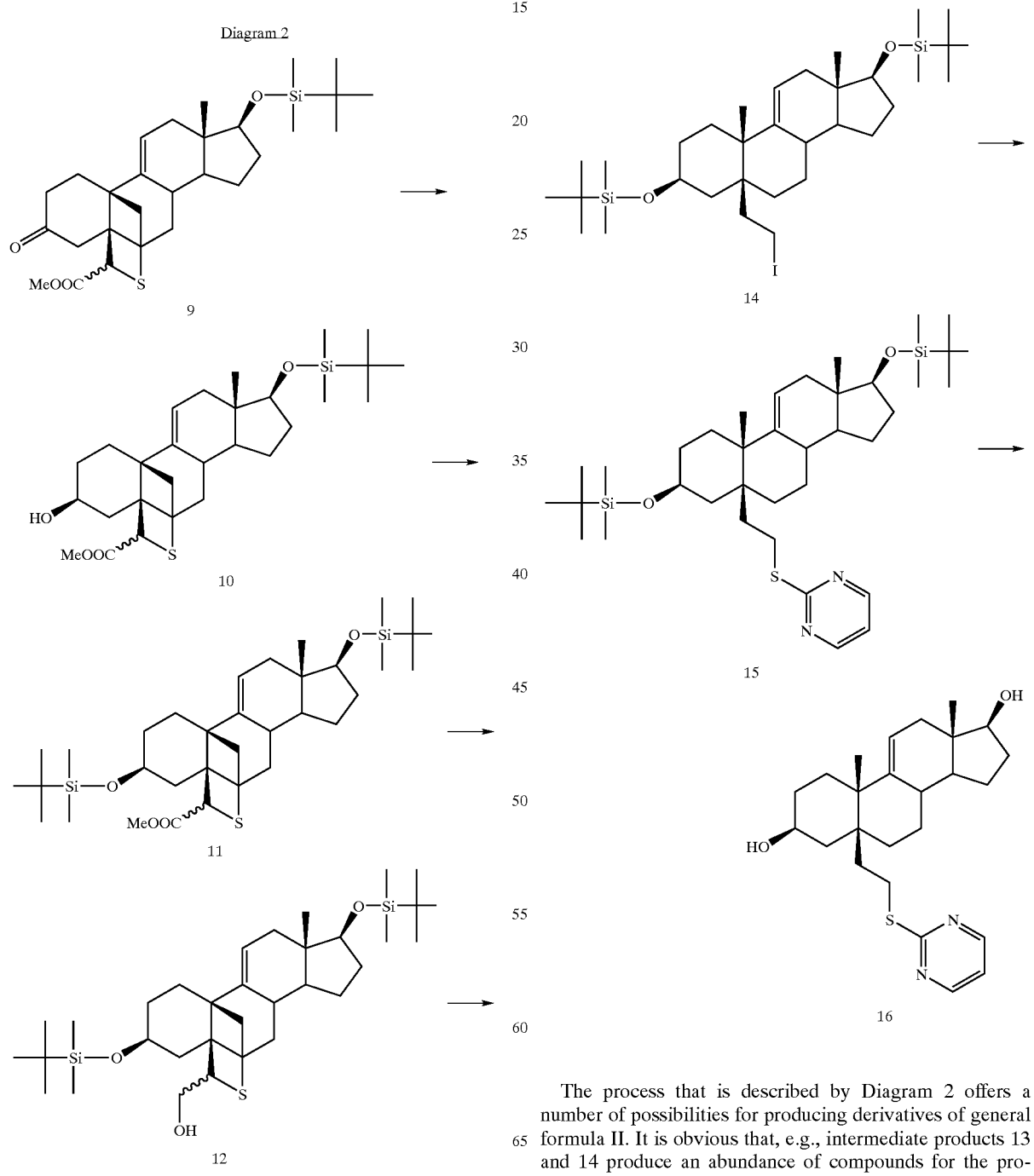

The process that is described by Diagram 2 offers a number of possibilities for producing derivatives of general formula II. It is obvious that, e.g., intermediate products 13 and 14 produce an abundance of compounds for the production of such new steroids.

The compounds of general formula II are a new class of antiandrogenically active steroids and thus are suitable for the treatment of androgen-dependent diseases (prostate carcinoma, prostate hyperplasia).

The subjects of the invention are therefore also the compounds of general formula II according to claim 12, process for their production according to claim 13 and their use according to claim 14.

The new compounds of general formula III are produced according to claim 17 from the 17β-silyl ether of general formula Ia.

The treatment of silylated iodide 8 of general formula Ia with a non-nucleophilic base (e.g., sodium hydride, triethylamine, fluoride) in an aprotic solvent (e.g., THF, DMF) results in the formation of cyclosteroid 18.

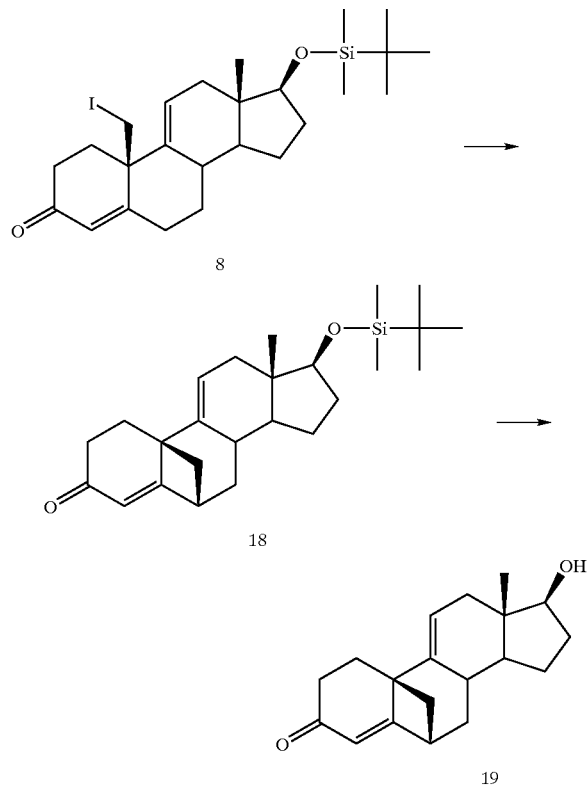

After conventional silyl ether cleavage (tetrabutylammonium fluoride), the new testosterone derivative 19, the 17β-hydroxy-6β,19-cycloandrosta-4,9(11)-dien-3-one, is produced. By standard processes (esterification, etherification, oxidation), 19 is converted in a simple way into additional compounds of general formula III, which are distinguished by aromatase- and 5α-reductase inhibiting action.

The subjects of the invention are consequently also the new 6β,19-cycloandrostadienes of formula III of claim 16, as well as processes for their production and their use according to claim 21.

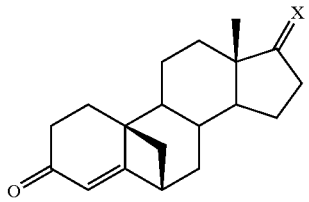

in which
X=O or the grouping 17β-OR, 17α-H, with R in the meaning of H, C1–C10-alkyl, C1–C10-acyl, whereby the acyl radical is derived from an aliphatic or aromatic carboxylic acid.

In addition, the subjects of the invention are the 17β-silyl ether of general formula Ia, which are produced as intermediate products from the compounds of general formula I according to the invention and common starting products for the new 5β-substituted steroids of general formula II and the 6β,19-cycloandrostadienes of Formula III.

The invention also includes pharmaceutical agents according to claim 24, which as active components contain at least one compound of general formula I, II and/or III.

The examples below are to explain the invention in more detail, without limiting the latter thereto.

EXAMPLE 1

17β-Hydroxy-19-iodo-androsta-4,9(11)-dien-3-one
a. 17β-(tert-Butyldimethylsilyloxy)-3,3-(2,2-dimethyl-trimethylenedioxy)-10β-formyl-androst-9(11)-en-5α-ol (2)

A solution of 5.0 g (12.4 mmol) of 3,3-(2,2-dimethyl-trimethylenedioxy)-10β-formyl-androst-9(11)-ene-5α,17β-diol is stirred after the addition of 3.43 g (50.4 mmol) of imidazole and 4.46 ml (14.7 mmol) of a 3.3 M solution of tert-butyldimethylchlorosilane in hexane for 16 hours at room temperature. For working-up, it is diluted with water and extracted with ethyl acetate. After chromatography on silica gel with hexane/ethyl acetate 1:9, 5.60 g (87.0% of theory) of the silyl ether is obtained with a melting point of 168–170° C. (hexane), [α]$_D$ −179.3° (CHCl$_3$, C≈0.5). $^1$H-NMR (CDCl$_3$, 300 MHz): δ=0.61 ppm (s, 3H, H-18); 0.87 (s, 9H, Si-tBu); 0.93 and 0.94 (2s; 3H, ketal-Me each); 3.63 (t, J=8 Hz, 1H, H-17); 4.45 (s, 1H, OH); 5.62 (m, 1H, H-11); 9.07 (s, 1H, CHO).

b. 17β-(tert-Butyldimethylsilyloxy)-3,3-(2,2-dimethyl-trimethylenedioxy)-androst-9(11)-ene-5α,19-diol (3)

A solution of 2.58 g (4.97 mmol) of the product, obtained under a., in 26 ml of THF and 26 ml of methanol is mixed at 0° C. with 211 mg (5.57 mmol) of sodium borohydride, and it is stirred for 1.5 hours at 0° C. After the addition of 105 mg (2.78 mmol) of NaBH$_4$ was again performed, it is stirred for another 75 minutes at 0° C., the reaction mixture was then stirred into ice water and extracted with ethyl acetate. The crystalline crude product (2.46 g, 95% of theory) is used without further purification in the next step. $^1$N-NMR (CDCl$_3$, 300 MHz): δ=0.67 ppm (s, 3H, H-18); 0.87 (s, 9H, Si-tBu); 0.93 and 0.99 (2s; 3H, ketal-Me each); 3.41–3.73 (m, 7H, CH$_2$OH, CH$_2$O, H-17); 4.51 (s, 1H, 5α-OH); 5.45 (d, J=7.5 Hz, 1H, H-11).

c. 17β-(tert-Butyldimethylsilyloxy)-3,3-(2,2-dimethyl-trimethylenedioxy)-19-iodo-androst-9(11)-en-5α-ol (4)

20.72 g (79.0 mmol) of triphenylphosphine and 5.38 g (79.0 mmol) of imidazole are added at room temperature to a solution of 16.07 g (30.9 mmol) of the alcohol, produced according to Example 1b, in 225 ml of THF. While being cooled with ice water, 10.03 g (39.5 mmol) of iodine is then added in portions over about 5 minutes to the reaction mixture and then stirred for 1.5 hours at ambient temperature (23° C.). For working-up, the reaction solution is poured into about 2 l of a 5% aqueous sodium thiosulfate solution, which was cooled to +5° C. and extracted with ethyl acetate. After chromatography of the crude product on silica gel with hexane/ethyl acetate 9:1, 17.0 g (87.2% of theory) of the iodide is obtained as a colorless oil. $^1$H-NMR (CDCl$_3$, 300 MHz) δ=0.80 ppm (s, 3H, H-18); 0.88 (s, 9H, Si-tBu); 0.92 and 2.00 (2s; 3H, ketal-Me each); 3.41–3.74 (m, 7H, CH$_2$I, CH$_2$O, H-17); 4.50 (s, 1H, 5α-OH); 5.30 (d, J=7.5 Hz, 1H, H-11).

d) 17β-(tert-Butyldimethylsilyloxy)-3,3-(2,2-dimethyltrimethylenedioxy)-19-iodo-androsta-5,9(11)-diene (5a) and 17β-(tert-butyldimethylsilyloxy)-3,3-(2,2-dimethyl-trimethylenedioxy)-19-iodo-androsta-4,9(11)-diene (5b)

The product that is obtained under Example 1c (16.95 g, 26.9 mmol) is dissolved in 85 ml of pyridine. While being cooled with ice water, 3.91 ml (53.8 mmol) of thionyl chloride is added in drops over about 15 minutes and stirred for 45 more minutes while being cooled with ice water. The thus produced yellow suspension is stirred into about 1 l of a mixture that consists of saturated common salt solution (500 ml) and saturated NaHCO$_3$ solution and extracted with ethyl acetate. The crude product that is obtained after the EE extracts are dried on Na$_2$SO$_4$ and concentrated by evaporation is taken up several times in toluene for the removal of pyridine radicals and concentrated by evaporation in a vacuum. In this way, 14.85 g of a crude mixture of the isomeric dehydration products, which is used without further purification in the subsequent reaction, is obtained.

e. 17β-Hydroxy-19-iodo-androsta-4,9(11)-dien-3-one (6)

A solution of 14.85 g (24.3 mmol) of the isomer mixture in 325 ml of dichloromethane and 32 ml of water that is obtained under 1d is stirred for 4 hours at room temperature after 64.6 ml (870 mmol) of trifluoroacetic acid is added. Then, it is diluted with 200 ml of dichloromethane, washed with saturated common salt solution and NaHCO$_3$ solution, dried on sodium sulfate and concentrated by evaporation. The crude product is chromatographed on silica gel with hexane/ethyl acetate 1:1, and after recrystallization of the main product from diisopropyl ether/ethyl acetate, it yields 6.62 g (66.1% of theory) of the title compound with a melting point of 146° C. (decomposition), [α]$_D$ −2.0° (CHCl$_3$, c=0.510). $^1$H-NMR (CDCl$_3$, 300 MHz): δ=0.87 ppm (s, 3H, H-18); 3.56 (AB-q, J=12 and 4 Hz, 2H, H-19); 3.78 (t, J=9 Hz, 1H, H-17); 5.60 (d, J=7.5 Hz, 1H, H-11); 5.85 (d, J=1.5 Hz, 1H, H-4).

EXAMPLE 2

19-Bromo-17β-hydroxy-androsta-4,9(11)-dien-3-one

Analogously to the procedure according to Example 1, the title compound with a melting point of 149° C. (decomposition), [α]$_D$ +20.4° (CHCl$_3$, c=0.509) is obtained when using elementary bromine instead of iodine in stage 1c after dehydration (analogously to Example 1d) and acid treatment (Example 1e). $^1$H-NMR (CDCl$_3$, 300 MHz): δ=0.80 pm (s, 3H, H-18); 3.64 (s, 2H, H-19); 3.77 (t, J=8 Hz, 1H, H-17); 5.64 (d, J=7.5 Hz, 1H, H-11); 5.89 (d, J=1 Hz, 1H, H-4).

EXAMPLE 3

17β-(tert-Butyldimethylsilyloxy)-3-oxo-2'H,5'H-thieno[3',4':5,10]-5β-estr-9(11)-ene-2'ξ-carboxylic acid methyl ester a. 17β-(tert-Butyldimethylsilyloxy)-19-iodo-androsta-4,9(11)-dien-3-one (8)

A reaction solution that consists of 7.36 g (17.9 mmol) of 17β-hydroxy-19-iodo-androsta-4,9(11)-dien-3-one, 7.48 g (110 mmol) of imidazole and 9.72 ml (32.1 mmol) of tert-butyldimethylchlorosilane (3.3 M in hexane) in 40 ml of DMF is stirred for 16 hours at room temperature and worked up as usual (Example 1a). 8.95 g (95% of theory) of the silyl ether is obtained. $^1$H-NMR (CDCl$_3$, 300 MHz): δ=0.82 ppm (s, 3H, H-18); 0.90 (s, 9H, Si-tBu); 3.57 (t, J=11 Hz, 2H, H-19); 3.68 (t, J=9 Hz, 1H, H-17); 5.59 (d, J=7.5 Hz, 1H, H-11); 5.85 (d, J=1.5 Hz, 1H, H-4).

b. 17β-(tert-Butyldimethylsilyloxy)-3-oxo-2'H,5'H-thieno[3',4':5,10]-5β-estr-9(11)-ene-2'ξ-carboxylic acid methyl ester 2.92 ml (32.2 mmol) of mercaptoacetic acid methyl ester is added in drops to a suspension of 1.38 g (46.1 mmol) of sodium hydride (80% in oil) in 92.5 ml of dimethylformamide while being cooled with ice water within 3 minutes, and it is stirred for another 15 minutes. Then, a solution of 8.95 g (17.7 mmol) of 17β-(tert-butyldimethylsilyloxy)-19-iodo-androsta-4,9(11)-dien-3-one in 111 ml of DMF is added drop by drop and stirred for 3 hours at room temperature. For working-up, it is poured into ice-cold saturated NH$_4$—Cl solution and extracted with ethyl acetate. After chromatography of the crude product on silica gel with hexane/ethyl acetate 3:1, 7.08 g (79.2% of theory) of the title compound is obtained as an isomer mixture on C-2'. $^1$H-NMR (CDCl$_3$, 300 MHz, 2'(R)-isomer): δ=0.62 ppm (s, 3H, H-18); 0.89 (s, 9H, Si-tBu); 3.42 and 3.68 (2d, J=10 Hz; 1H, H-19 each); 3.70 (t, J=9 Hz, 1H, H-17); 3.75 (s, 3H, COOMe); 4.01 (s, 1H, H-2'); 5.83 (d, J=7.5 Hz, 1H, H-11).

EXAMPLE 4

5-[2-(2-Pyrimidylsulfanyl)-ethyl]-5β-androst-9(11)-ene-3β,17β-diol (16)

a. 17β-(tert-Butyldimethylsilyloxy)-3β-hydroxy-2'H,5'H-thieno[3',4':5,10]-5β-estr-9(11)-ene-2'ξ-carboxylic acid methyl ester (10)

4.36 g (17.1 mmol) of lithium-tri-tert-butoxyaluminum hydride is added in portions to a solution of 3.20 g (6.34 mmol) of the isomer mixture, obtained under Example 3b, in 69 ml of THF while being cooled with ice water. After the addition, it is stirred for 3 hours at room temperature, excess reducing agent is decomposed by careful addition of about 15 ml of water, it is filtered on Celite, the filtrate is poured into about 300 ml of 5% aqueous ammonium chloride solution and extracted with ethyl acetate. The crude product is chromatographed on silica gel with hexane/ethyl acetate 2:1 and yields 2.35 (73.1% of theory) of the reduction product.

b. 3β,17β-Bis-(tert-butyldimethylsilyloxy)-2'H,5'H-thieno[3',4':5,10]-5β-estr-9(11)-ene-2'ξ-carboxylic acid methyl ester (11)

From 2.35 g (4.64 mmol) of the reduction product that is obtained under 4a, 2.41 g (35.4 mmol) of imidazole and 3.14 ml (10.4 mmol) of a 3.3 M hexane solution of tert-butyldimethylchlorosilane in 10.2 ml of DMF, 2.67 g (92.6% of theory) of the silyl ether is obtained under the conditions of Example 2a.

c. 3β,17β-Bis-(tert-butyldimethylsilyloxy)-2'H,5'H-thieno[3',4':5,10]-5β-estr-9(11)-ene-2'ξ-methanol (12)

A solution of 2.67 g (4.50 mmol) of the product, obtained under Example 4b, in 12.3 ml of THF is added in drops to a suspension of 193 mg (5.09 mmol) of lithium aluminum hydride in 5.4 ml of THF while being cooled with ice water. It is stirred for 2.5 hours while being cooled with ice water, then excess LiAlH$_4$ is decomposed by careful addition of 2 ml of water, it is stirred for another 30 minutes at room temperature, filtered on Celite, the filter reside is washed with THF and ethyl acetate, the filtrate is taken up in about 300 ml of water, and the ethyl acetate phase is separated.

After thorough re-extraction of the aqueous phase with ethyl acetate, the EE extracts are combined, dried on $Na_2SO_4$ and concentrated by evaporation. The thus obtained crude product (2.36 g, 100% of theory) is used without further purification in the next step.

For analytical purposes, a sample of the crude product that consists of ethanol is recrystallized. In this way, the 2'(R)-isomer can be obtained in a pure state. Melting point 177° C., $[\alpha]_D$ +16.3° ($CHCl_3$, C=0.516). $^1$H-NMR ($CDCl_3$, 300 MHz): δ=0.62 ppm (s, 3H, H-18); 0.88 and 0.90 (2s; 9H, Si-tBu each); 2.25 and 3.22 (2d, J=10 Hz; 1H, H-19 each); 3.65 (t, J=9 Hz, 1H, H-17); 3.70 and 3.87 (2m; 1H, $CH_2OH$ each); 4.06 (s(br), 1H, H-3); 4.95 (q, J=6 and 2 Hz, 1H, H-2'); 5.59 (d, J=7.5 Hz, 1H, H-11).

d. 3β,17β-Bis-(tert-butyldimethylsilyloxy)-5-(2-hydroxyethyl)-5β-androst-9(11)-ene (13)

A suspension of 2.36 g (3.98 mmol) of the product that is obtained above and 10 g of Raney nickel in 92 ml of ethanol is refluxed for 3 hours. After cooling, the reaction solution is mixed with 100 ml of dichloromethane and filtered on Celite. The filter residue is washed thoroughly with dichloromethane. After the filtrate is concentrated by evaporation, a crude product of 2.36 g, which is chromatographed on silica gel with hexane/ethyl acetate, remains. The main fraction yields 1.88 g (83.9% of theory) of the crystalline desulfurization product.

e. 3β,17β-Bis-(tert-butyldimethylsilyloxy)-5-(2-iodoethyl)-5β-androst-9(11)-ene (14)

Under the conditions of Example 1c, 1.85 g (82.3% of theory) of the iodide is obtained from 1.88 g (3.34 mmol) of the alcohol that is formed under 4d, 2.24 g (8.53 mmol), 580 mg (8.53 mmol) of imidazole and 1.09 g (4.29 mmol) of iodine in 24.3 ml of THF after analogous implementation and working-up. $^1$H-NMR ($CDCl_3$, 300 MHz): δ=0.64 ppm (s, 3H, H-18); 0.88 and 0.93 (2s; 9H, Si-tBu each); 0.99 (s, 3H, H-19); 3.20 and 3.42 (2m; 1H, $CH_2I$ each); 3.63 (t, J=9 Hz, 1H, H-17); 4.05 (s(br), 1H, H-3); 5.42 (d, J=7.5 Hz, 1H, H-11).

f. 3β,17β-Bis-(tert-butyldimethylsilyloxy)-5-[2-(2-pyrimidylsulfanyl)-ethyl]-5β-androst-9(11)-ene (15)

A suspension of 111 mg (2.54 mmol) of NaH (55% in oil) in 5 ml of DMF is stirred after the addition of 199 mg (1.77 mmol) of pyrimidine-2-thiol for 15 minutes at room temperature and then mixed drop by drop with a solution of 655 mg (0.97 mmol) of the iodide that is obtained above in 6 ml of THF and 6 ml of diethyl ether. It is stirred for 21 hours at ambient temperature, poured into ice-cold, saturated NaCl solution and extracted with ethyl acetate. After chromatography on silica gel with hexane/ethyl acetate 9:1, 600 mg (93.8% of theory) of the crystalline substitution product is obtained.

g. 5-[2-(2-Pyrimidylsulfanyl)-ethyl]-5β-androst-9(11)-ene-3β,17β-diol (16)

A solution of 590 mg (0.89 mmol) of the product, obtained under Example 4f, in 26.1 ml of THF is stirred for 8 hours at 60° C. after the addition of 2.76 g (8.74 mmol) of tetrabutylammonium fluoride ($Bu_4NF.3H_2O$). After cooling, it is poured into saturated $NaHCO_3$ solution and extracted with ethyl acetate. After chromatography on silica gel with hexane/ethyl acetate 4:1 and recrystallization of the main product that consists of ethanol/diisopropyl ether, 250 mg (67.5% of theory) of the title compound with a melting point of 209° C., $[\alpha]_D$ -27.4° (MeOH, C=0.507) is obtained. $^1$H-NMR (DMSO-$d_6$, 300 MHz): δ=0.59 ppm (s, 3H, H-18); 0.93 (s, 3H, H-19); 3.56 (m, 1H, H-17); 3.93 (s(br), 1H, OH); 4.30 (s(br), 1H, H-3); 4.40 (m, 1H, OH); 5.46 (d, J=7.5 Hz, 1H, H-11); 7.17 (t, J=5 Hz, 1H, H-5'); 8.60 (d, J=5 Hz, 2H, H-4' and H-6').

When using the corresponding thiols, additional end products are obtained according to the process of Example 4:

1. 5-[2-(Heptylsulfanyl)-ethyl]-5β-androst-9(11)-ene-3β,17β-diol, melting point 126° C. (hexane/ethyl acetate), $[\alpha]_D$ +15.0° ($CHCl_3$, c=0.453).
2. 5-[2-[(1-ethyl-1H-imidazole-2-yl)sulfanyl]ethyl]-5β-androst-9(11)-ene-3β,17β-diol, melting point 212° (hexane/ethyl acetate), $[\alpha]_D$ +85.5° ($CHCl_3$, c=0.503). $^1$H-NMR ($CDCl_3$, 300 MHz): δ=0.69 ppm (s, 3H, H-18); 1.01 (s, 3H, H-19); 3.55 (s, 3H, Nme); 3.74 (t, J=8 Hz, 1H, H-17); 5.48 (m, 1H, H-11); 6.87 (d, J=0.5 Hz, 1H, imidazole-H); 7.00 (d, J=0.5 Hz, 1H, imidazole-H).
3. 5-[2-(Benzothiazole-2-yl)-sulfanyl]-5β-androst-9(11)-ene-3β,17β-diol, $[\alpha]_D$ +99.0° ($CHCl_3$, c=0.5). $^1$H-NMR ($CDCl_3$, 300 MHz): δ=0.69 ppm (s, 3H, H-18); 1.01 (s, 3H, H-19); 4.18 (s, 1H, H-3); 5.50 (m, 1H, H-11); 7.27 (dd, J=7.5 and 8 Hz, 1H, arom.-H); 7.41 (dd, J=7.5 and 8 Hz, 1H, arom.-H); 7.73 (d, J=7.5 Hz, 1H, arom.-H); 7.88 (d, J=7.5 Hz, 1H, arom.-H).
4. 5-[2-(Thiene-2-yl)-sulfanyl]ethyl-5β-androst-9(11)-ene-3β,17β-diol, melting point 156° C. $[\alpha]_D$ +3.0° ($CHCl_3$, c=0.47). $^1$H-NMR ($CDCl_3$, 300 MHz): δ=0.65 ppm (s, 3H, H-18); 0.99 (s, 3H, H-19); 2.75 (m, 1H, $CH_2S$); 3.08 (m, 1H, $CH_2S$); 3.72 (t, J=8 Hz, 1H, H-17); 4.06 (s(br), 1H, H-3); 5.45 (m, 1H, H-11); 6.95 (dd, J=4 and 7 Hz, 1H, thienyl-H); 7.12 (dd, J=1 and 4 Hz, 1H, thienyl-H); 7.32 (dd, J=1 and 7 Hz, 1H, thienyl-H).

EXAMPLE 5

5-Ethyl-5β-androst-9(11)-ene-3β,17β-diol

A solution of 2.25 g (3.34 mmol) of 3β,17β-bis-(tert-butyldimethylsilyloxy)-5-(2-iodoethyl-5β-androst-9(11))-ene (Example 4e) is heated to 80° C. after the addition of 50 mg of azobisisobutyronitrile and mixed drop by drop with 2 ml of tributyltin hydride. It is stirred for another 60 minutes at 80° C. and poured after cooling into 150 ml of a 5% aqueous sodium fluoride solution. The crude product that is obtained after extraction with ethyl acetate is treated with tetrabutylammonium fluoride in THF under the conditions of Example 1g. After chromatography, 720 mg (67.8%) of the title compound with a melting point of 165° C. (hexane/ethyl acetate) is obtained. $[\alpha]_D$ +18.8° ($CHCl_3$, c=0.493).

EXAMPLE 6

3β,17β-Dihydroxy-5β-androst-9(11)-ene-5-propanenitrile a. 3β,17β-Bis-(tert-butyldimethylsilyloxy)-5β-androst-9(11)ene-5-propanenitrile A suspension of 2.23 g (3.31 mmol) of 3β,17β-bis-(tert-butyldimethylsilyloxy)-5-(2-iodoethyl)-5β-androst-9(11)-ene (Example 4e) and 948 mg (15.11 mmol) of KCN in 48 ml of DMF is stirred for 36 hours at 60° C. under argon. After cooling, it is poured into ice-cold 1N NaOH solution and extracted with dichloromethane. After chromatography of the crude product on silica gel with hexane/ethyl acetate, 1.56 g (75.5% of theory) of the nitrile with a melting point of 194–195° C. (hexane), $[\alpha]_D$ +15.0° ($CHCl_3$, c=0.5), is obtained.

a. 3β,17β-Dihydroxy-5β-androst-9(11)-ene-5-propanenitrile

A solution of 300 mg (0.52 mmol) of the nitrile above in 30 ml of THF is stirred for 2 hours at 60° C. after the addition of 2.67 g (10.3 mmol) of tetrabutylammonium fluoride and worked up under the conditions of Example 1g. After crystallization from hexane/ethyl acetate, 140 mg (77.8%) with a melting point of 203° C., $[\alpha]_D$ +20.9°

(CHCl₃, c=0.496), is obtained. ¹H-NMR (CDCl₃, 300 MHz): δ=0.69 ppm (s, 3H, H-18); 1.01 (s, 3H, J-19); 2.52–2.75 (m, 2H, CH₂CN); 3.73 (t, J=8 Hz, 1H, H-17); 4.10 (s(br), 1H, H-3); 5.48 (m, 1H, H-11).

EXAMPLE 7

17β-Hydroxy-6β,19-cycloandrosta-4,9(11)-dien-3-one a. 17β-(tert-Butyldimethylsilyloxy)-6β,19-cycloandrosta-4,9(11)-dien-3-one (18)

A suspension of 650 mg (14.9 mmol) of NaH (55% in oil) in 30 ml of DMF is mixed at room temperature drop by drop with a solution of 3.00 g (5.70 mmol) of 17β-(tert-butyldimethylsilyl-oxy)-19-iodo-androsta-4,9(11)-dien-3-one (8) in 35 ml of DMF and 6.5 ml of diethyl ether. It is stirred for 2.5 hours at 25° C., then poured into ice-cold, saturated NaCl solution and extracted with ethyl acetate. After chromatographic purification, 1.98 g (79.2% of theory) of crystalline 17β-(tert-butyldimethylsilyl-oxy)-6β,19-cycloandrosta-4,9(11)-dien-3-one is obtained.

b. 17β-Hydroxy-6β,19-cycloandrosta-4,9(11)-dien-3-one (19)

A solution of 680 mg (1.33 mmol) of the product that is obtained above and 4.09 g (13.0 mmol) of tetrabutylammonium fluoride (Bu₄NF.3H₂O) is stirred for 2 hours at 60° C. After working-up analogously to Example 3g and chromatography of the crude product on silica gel with ethyl acetate, 370 mg (97.8% of theory) of the title compound is obtained. Recrystallization of a sample that consists of hexane/ethyl acetate yields colorless crystals with a melting point of 176–179° C., [α]$_D$ −232.9° (CHCl₃, c=0.502). ¹H-NMR (CDCl₃, 300 MHz) δ=0.80 ppm (s, 3H, H-18); 3.78 (t, J=9 Hz, 1H, H-17); 5.60 (m, 2H, H-4 and H-11).

EXAMPLE 8

6β,19-Cycloandrost-4,9(11)-diene-3,17-dione

A solution of 450 mg (1.58 mmol) of the alcohol that is obtained under Example 7b is mixed drop by drop with 0.98 ml of Jones reagent while being cooled with ice water, and it is stirred for 60 more minutes at room temperature. Then, it is poured into 5% aqueous sodium thiosulfate solution and extracted with ethyl acetate. After chromatography on silica gel and crystallization from hexane/ethyl acetate, 138 mg (30.9%) of the ketone with a melting point of 139° C., [α]$_D$ −109.2° (CHCl₃, c=0.511), is obtained. ¹H-NMR (CDCl₃, 300 MHz): δ=0.95 ppm (s, 3H, H-18); 3.33 (t, J=6 Hz, 1H, H-6); 5.64 (m, 2H, H-4, H-11).

What is claimed is:

1. A compound of formula II

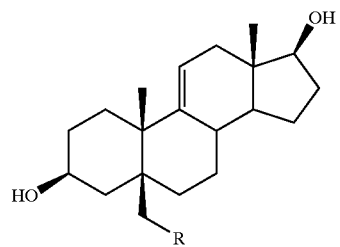

wherein radical R is:
—(CH₂)$_n$—CH₂—R¹, —(CH₂)$_n$—CH₂—OR¹,
—(CH₂)$_n$—CH₂—OCOR¹, —(CH₂)$_n$—CH₂—SR¹,
—(CH₂)$_n$—CH₂—NR¹R², —(CH₂)$_n$—CHO,
—(CH₂)$_n$—CN, in which n can assume the values of 0–5, and radicals R¹ and R², independently of one another, stand for hydrogen or a straight-chain or branched, saturated or unsaturated hydrocarbon radical with up to 18 C atoms, whereby this radical optionally can contain additional functional groups and carbocyclic or heterocyclic ring elements.

2. A compound according to claim 1, wherein R is an ethyl group.

3. A compound according to claim 1, wherein R is 2-(2-pyrimidylsulfanyl)-ethyl, 2-(heptylsulfanyl)-ethyl, 2-[(1-methyl-1H-imidazole-2-yl)sulfanyl]ethyl, 2-(benzothiazole-2-yl)-sulfanyl, or [2-(thiene-2-yl)-sulfanyl]ethyl.

4. A composition comprising a compound according to claim 1 and a pharmaceutically acceptable carrier.

5. A method of treating an androgen-dependent disease, comprising administering an effective amount of a compound according to claim 1 to a patient in need thereof.

6. A process for the production of 5β-substituted androst-9(11)-enes of general formula II according to claim 12 by reaction of a compound of general formula I:

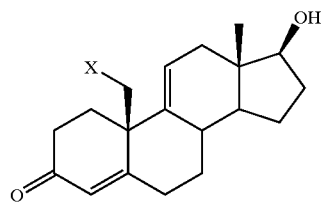

in which X=halogen selected from Br and I and further reaction with mercaptoacetic acid methyl ester for the formation of 17β-silylated-3-oxo-2'H,5'H-thieno[3',4':5,10]-5β-estr-9(11)-ene-2'ξ-carboxylic acid methyl ester, which then is reacted to form a target compound of Formula II:

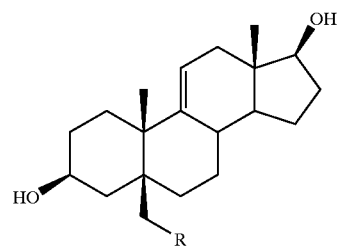

wherein radical R is:
—(CH₂)$_n$—CH₂—R¹, —(CH₂)$_n$—CH₂—OR¹,
—(CH₂)$_n$—CH₂—OCOR¹, —(CH₂)$_n$—CH₂—SR¹,
—(CH₂)$_n$—CH₂—NR¹R², —(CH₂)$_n$—CHO,
—(CH₂)$_n$—CN, in which n can assume the values of 0–5, and radicals R¹ and R², independently of one another, stand for hydrogen or a straight-chain or branched, saturated or unsaturated hydrocarbon radical with up to 18 C atoms, whereby this radical optionally can contain additional functional groups and carbocyclic or heterocyclic ring elements.

* * * * *

UNITED STATES PATENT AND TRADEMARK OFFICE
CERTIFICATE OF CORRECTION

PATENT NO. : 6,790,843 B1
DATED : September 14, 2004
INVENTOR(S) : Neef et al.

It is certified that error appears in the above-identified patent and that said Letters Patent is hereby corrected as shown below:

Column 16,
Line 22, reads "claim 12" should read -- claim 1 --.

Signed and Sealed this

First Day of February, 2005

JON W. DUDAS
*Director of the United States Patent and Trademark Office*